US010973435B2

(12) United States Patent
Schiff et al.

(10) Patent No.: US 10,973,435 B2
(45) Date of Patent: Apr. 13, 2021

(54) ADULT HEAD-SIZED COIL-BASED LOW-FIELD MRI

(71) Applicants: The Penn State Research Foundation, University Park, PA (US); TRIAD NATIONAL SECURITY, LLC, Los Alamos, NM (US)

(72) Inventors: Steven J. Schiff, State College, PA (US); Johnes Obungoloch, Mbarara (UG); Joshua Harper, Boalsburg, PA (US); Srinivas Tadigadapa, Newton, MA (US); Igor Savukov, Los Alamos, NM (US)

(73) Assignees: THE PENN STATE RESEARCH FOUNDATION, University Park, PA (US); TRIAD NATIONAL SECURITY, LLC, Los Alamos, NM (US)

(*) Notice: Subject to any disclaimer, the term of this patent is extended or adjusted under 35 U.S.C. 154(b) by 12 days.

(21) Appl. No.: 16/608,265

(22) PCT Filed: Apr. 27, 2018

(86) PCT No.: PCT/US2018/029873
§ 371 (c)(1),
(2) Date: Oct. 25, 2019

(87) PCT Pub. No.: WO2018/201001
PCT Pub. Date: Nov. 1, 2018

(65) Prior Publication Data
US 2020/0121213 A1 Apr. 23, 2020

Related U.S. Application Data

(60) Provisional application No. 62/491,388, filed on Apr. 28, 2017.

(51) Int. Cl.
*G01R 33/44* (2006.01)
*A61B 5/055* (2006.01)
(Continued)

(52) U.S. Cl.
CPC ............ *A61B 5/055* (2013.01); *G01R 33/385* (2013.01); *G01R 33/4215* (2013.01); *G01R 33/445* (2013.01); *A61M 2210/06* (2013.01)

(58) Field of Classification Search
CPC .. A61B 5/055; G01R 33/385; G01R 33/4215; G01R 33/445; G01R 33/422; A61M 2210/06
See application file for complete search history.

(56) References Cited

U.S. PATENT DOCUMENTS 6,275,039 B1 * 8/2001 Young ................ G01R 33/3808
324/300
6,885,192 B2 4/2005 Clarke et al.
(Continued)

*Primary Examiner* — G. M. A Hyder
(74) *Attorney, Agent, or Firm* — Dinsmore & Shohl LLP

(57) ABSTRACT

An ultra-low field pre-pulse Magnetic Resonance Imaging (PMRI) system for a head includes RF coils defining a bore for head access, a pre-pulse coil outside the RF coils, and a coil assembly including a main magnetic field coil and gradient coils outside the pre-pulse coil. The PMRI system includes a first cylindrical shield concentric with the RF coils and made from conductive materials. The first cylindrical shield partially encloses the RF coils and inside the pre-pulse coil for shielding the RF coils from environmental electromagnetic disturbances.

11 Claims, 14 Drawing Sheets

(51) Int. Cl.
*G01R 33/385* (2006.01)
*G01R 33/421* (2006.01)

(56) References Cited

U.S. PATENT DOCUMENTS

| | | |
|---|---|---|
| 2004/0066194 A1 | 4/2004 | Slade et al. |
| 2011/0118588 A1 | 5/2011 | Komblau et al. |
| 2012/0001631 A1* | 1/2012 | Espy .................... G01R 33/448 |
| | | 324/309 |
| 2013/0144153 A1* | 6/2013 | Inglis .................... A61B 5/055 |
| | | 600/409 |
| 2014/0084925 A1 | 3/2014 | Nieminen et al. |
| 2014/0111202 A1* | 4/2014 | Wald .................... G01R 33/383 |
| | | 324/309 |
| 2014/0343397 A1 | 11/2014 | Kim et al. |
| 2019/0082997 A1* | 3/2019 | Lee .................... G01R 33/445 |

* cited by examiner

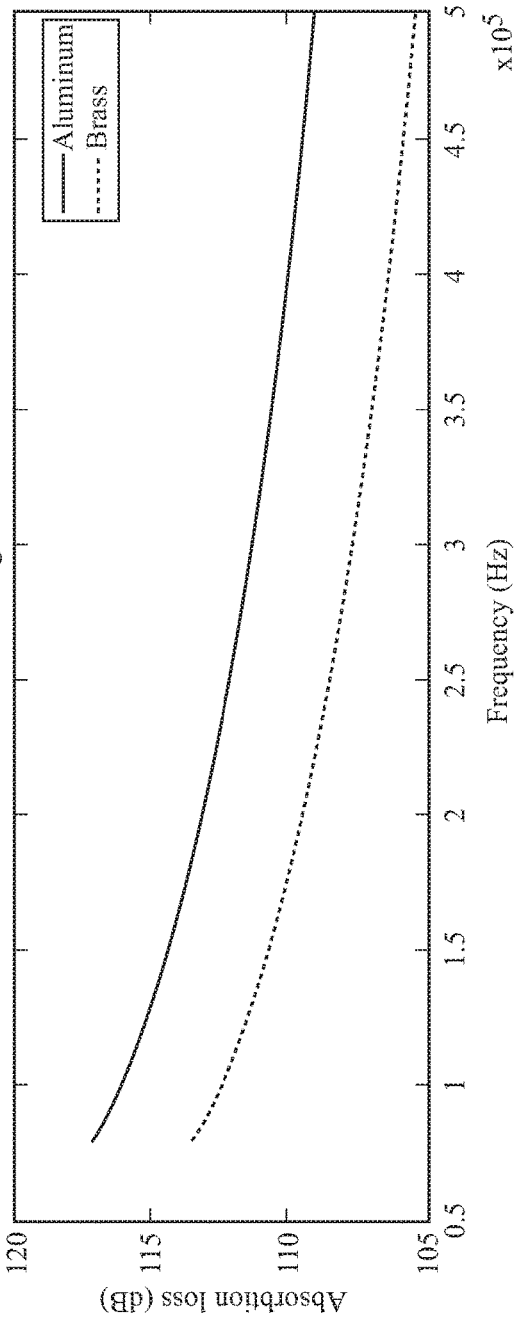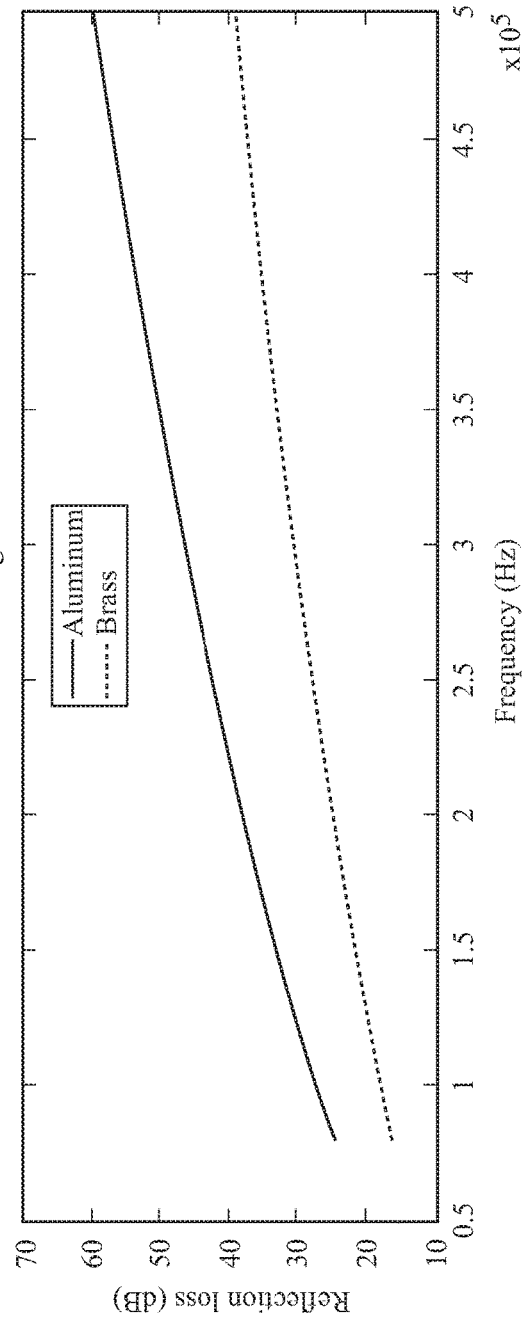

ADULT HEAD-SIZED COIL-BASED LOW-FIELD MRI

REFERENCE TO RELATED APPLICATION

This application is as U.S. national stage application of PCT/US2018/029873, filed Apr. 27, 2018, which claims priority to U.S. Provisional Application No. 62/491,388 filed Apr. 28, 2017, the entire content of which is incorporated herein by reference

GOVERNMENT SPONSORSHIP

This invention was made with government support under Contract No. 8923331CNA000001 awarded by U.S. Department of Energy/National Nuclear Safety Administration and under Grant No. HD086071 awarded by the National institutes of Health. The government has certain right in the invention.

FIELD OF THE INVENTION

The present invention relates generally to a pre-pulsed ultra-low field magnetic resonance imaging system and its self-contained shielding system.

BACKGROUND OF THE INVENTION

The need for affordable and appropriate medical technologies for developing countries continue to rise as challenges such as inadequate energy supply, limited technical expertise and poor infrastructure persist.

Hydrocephalus is a common condition in children planetwide that requires brain imaging and neurosurgical treatment. It is estimated that there are as many as 300,000 new cases per year throughout sub-Saharan Africa (SSA).

Hydrocephalus in infancy also presents one of the most straightforward challenges for imaging. In these cases, the most important task is to segment an image of the head into brain and cerebrospinal fluid (CSF). The requirements for tissue contrast within the brain are not important for initial diagnostics and treatment. Similarly, the spatial resolution required to affect treatment decisions are low-fluid compartments of at least multiple cubic centimeters in volume must be identified for fenestration or drainages. Although most new cases are seen in infancy, the heads can readily grow to adult size early in the first year of life. Nevertheless, the small infant body permits designs of imaging systems far smaller than that required for adult imaging.

Magnetic resonance imaging (MRI) is arguably the safest imaging method technology for brain imaging, that can be used to guide the treatment of hydrocephalus, but it is also the most expensive structural brain imaging modality available. Conventional high field (HF) MRI uses very strong magnetic fields produced by super-conducting magnets, cooled by liquid helium and nitrogen. Additionally, HF MRI systems must be shielded from external electromagnetic fields using high permeability materials. The high cost, which can be over $1 million for just installation of a 1.5 T whole body MRI scanner, high power requirements, stringent technical demands and strict infrastructure specifications have hindered the proliferation of HF MRI in developing countries. As a less expensive option, developing countries more often use computed tomography (CT) for brain imaging. While this alleviates many of the difficulties of HF MRI, CT delivers relatively high doses of ionizing radiation which are especially harmful to young infants.

SUMMARY OF THE INVENTION

The present invention provides an ultra-low field MRI with self-contained shielding suitable for the diagnosis of hydrocephalus in the developing world. Parameters considered for the suitability of this MRI include low cost, low power and technical requirements, portability and flexibility in siting.

It is noted that the high tissue contrast and fine spatial resolution provided by typical CT or HF MRI substantially exceeds what is required to reach surgical management decisions and achieve good patient outcomes in hydrocephalus. Low field (LF) coil based MRI systems can offer an affordable, sustainable, and safe imaging alternative to HF MRI and CT for brain imaging, in developing countries by reducing costs in both materials and manufacturing, reducing power requirements, eliminating the need for specialized equipment housing, and simplifying the technical aspects of troubleshooting, operation, and repair. The introduction of pre-pulse MRI (PMRI) technology by Conolly et al. in 1993 expanded the potential benefits offered by LF MRI technology. The pre-pulse MRI uses two separately optimized electromagnet systems to provide a weak static and homogeneous magnetic field (Bm) at which the image is acquired, and a relatively strong pulsating magnetic field (Bp) to provide additional polarization for the proton spins before image acquisition. This technique allows acquisition of a MR signal at very low frequencies provided by the Bm field while taking advantage of the high signal to noise ratio (SNR) provided by the Bp field. Other advantages of this technology include a low power requirement and relaxation, of the magnetic field homogeneity requirements especially for the stronger Bp field.

Magnetic resonance imaging (MRI) is very sensitive to magnetic and electrical interference (noise) which can greatly degrade the MRI signal. Conventional MRI systems require special suites specifically constructed with materials to shield unwanted electromagnetic signals. The cost of constructing these special suites can be as high as $3750 per square foot. To minimize this cost, low field MRI systems are designed to operate in, minimally shielded environments. The shielding materials used in low field MRI have therefore to be inexpensive.

In order to meet this aim, internal shielding rather than external shielding is preferred to obtain the mobility, portability and affordability of the PMRI device.

The present invention provides an ultra-low field PMRI system for head imaging, including annular RF coils defining a bore for head access, an annular pre-pulse coil surrounding the RF coils, and a coil assembly surrounding the pre-pulse coil including a main magnetic field coil and a plurality of gradient coils. The coils may be concentric with one another. The ultra-low field PMRI system may further include a first cylindrical shield concentric with the RF coils, the first cylindrical shield partially surrounding the RF coils and being disposed inside the pre-pulse coil for shielding the RF coils from environmental electromagnetic disturbances. The first cylindrical shield may be made from conductive materials.

In some versions, the PMRI system may further include a second cylindrical shield concentric with the first cylindrical shield and partially surrounding the pre-pulse coil and being disposed inside the coil assembly.

The PMRI system may further include a third cylindrical shield concentric with the first and second cylindrical shields and substantially surrounding the coil assembly.

The integration of the concentric shields renders the PMRI system self-contained.

The third cylindrical shield need not be solid and may include a wall formed of spaced bars. The third cylindrical shield may be made from ferromagnetic materials.

In some versions, the cylindrical shields may have an open end that is flared to accommodate a larger child or adult with shoulders wider than the bore.

In some other versions, the first cylindrical shield may have an open end for the head access and a capped end away from the open end All of the cylindrical shields may be passive and grounded.

In some versions, all of the cylindrical shield may be active and driven adaptively.

Materials with high permeability are preferred. The materials with less permeability may be used provided the frequency of the magnetic field is high enough to generate eddy currents on the surface of the materials. In a preferred embodiment, aluminum or brass can be used for shielding.

BRIEF DESCRIPTION OF THE DRAWINGS

FIG. 6A is a graphical illustration of absorption loss in aluminum and brass;

FIG. 6B is a graphical illustration of reflection loss in aluminum and brass;

DETAILED DESCRIPTION OF THE INVENTION

Overview

The present invention provides an ultra-low field MRI with self-contained shielding suitable for the diagnosis of hydrocephalus in the developing world.

Figure 1:
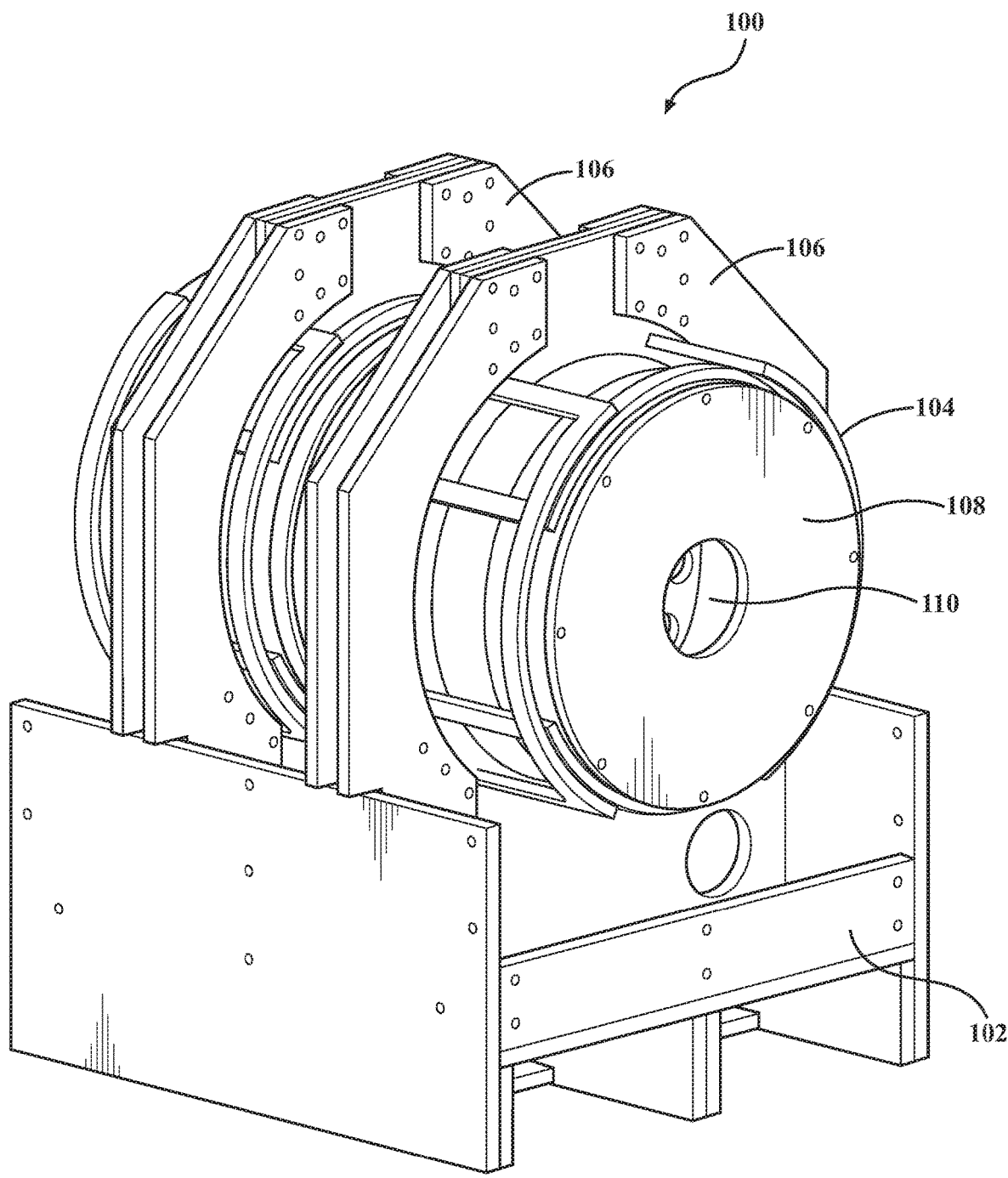
FIG. 1 is a perspective view of a pre-pulsed magnetic resonance imaging (PMRI) system in accordance with an embodiment of the present invention.
Figure 2:
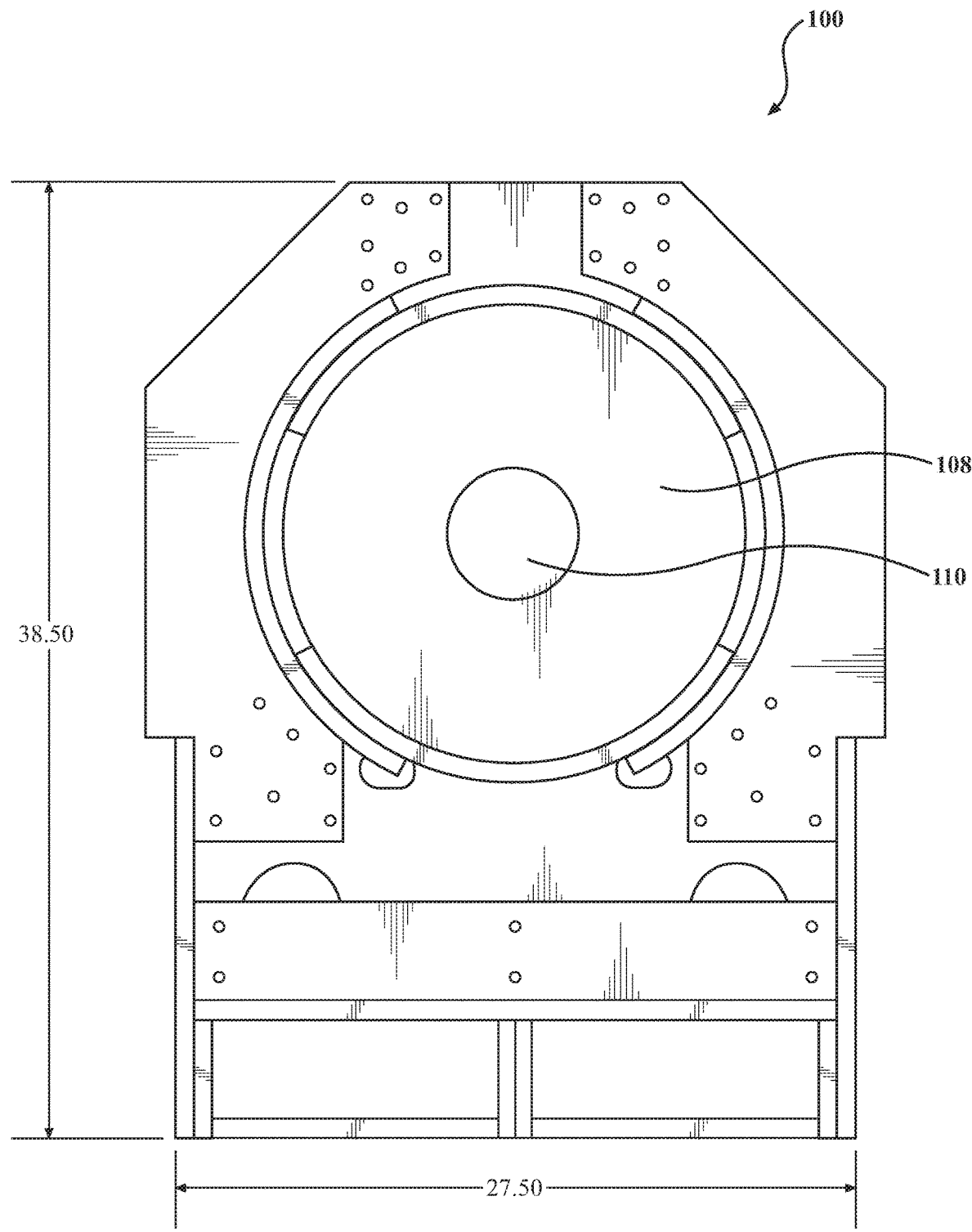
FIG. 2 is an elevational view of the PMRI system in accordance with an embodiment of the present invention.
Figure 3:
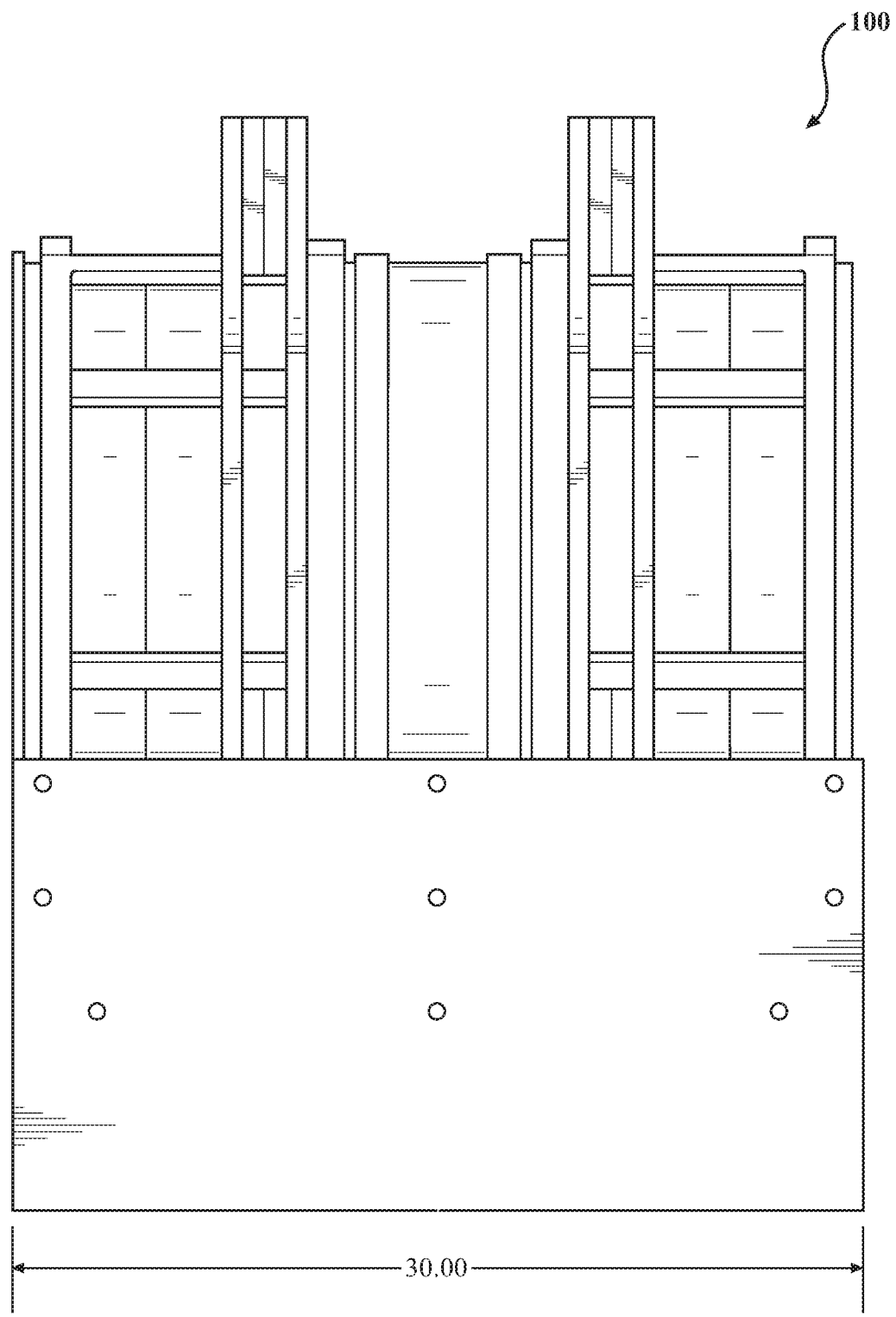
FIG. 3 is a side view of the PMRI system in accordance with an embodiment of the present invention.

In one example, an ultra-low field MRI system capable of admitting an adult head was constructed at a cost of $30,000. This MRI system requires no cryogens, has maximum power requirement of 1.5 kW, weighs 125 kg and can operate in an un-shielded room. Images of vegetables were acquired with the system operated at 113 kHz. FIGS. 1, 2 and 3 are a perspective view, an elevational view, and a side view, respectively, of a PMRI system in accordance with an embodiment of the present invention respectively. In this embodiment, the PMRI system include a generally cylindrical assembly 104 supported by two, support structures 106 and rested on a base 102. The support structures 106 may be parallel to each other and placed around the body of the assembly 104. The assembly 104 may have two ends 108 parallel to each other. One end may have an opening 110 for head access. The other end may have a similar opening or may be capped.

Figure 4:
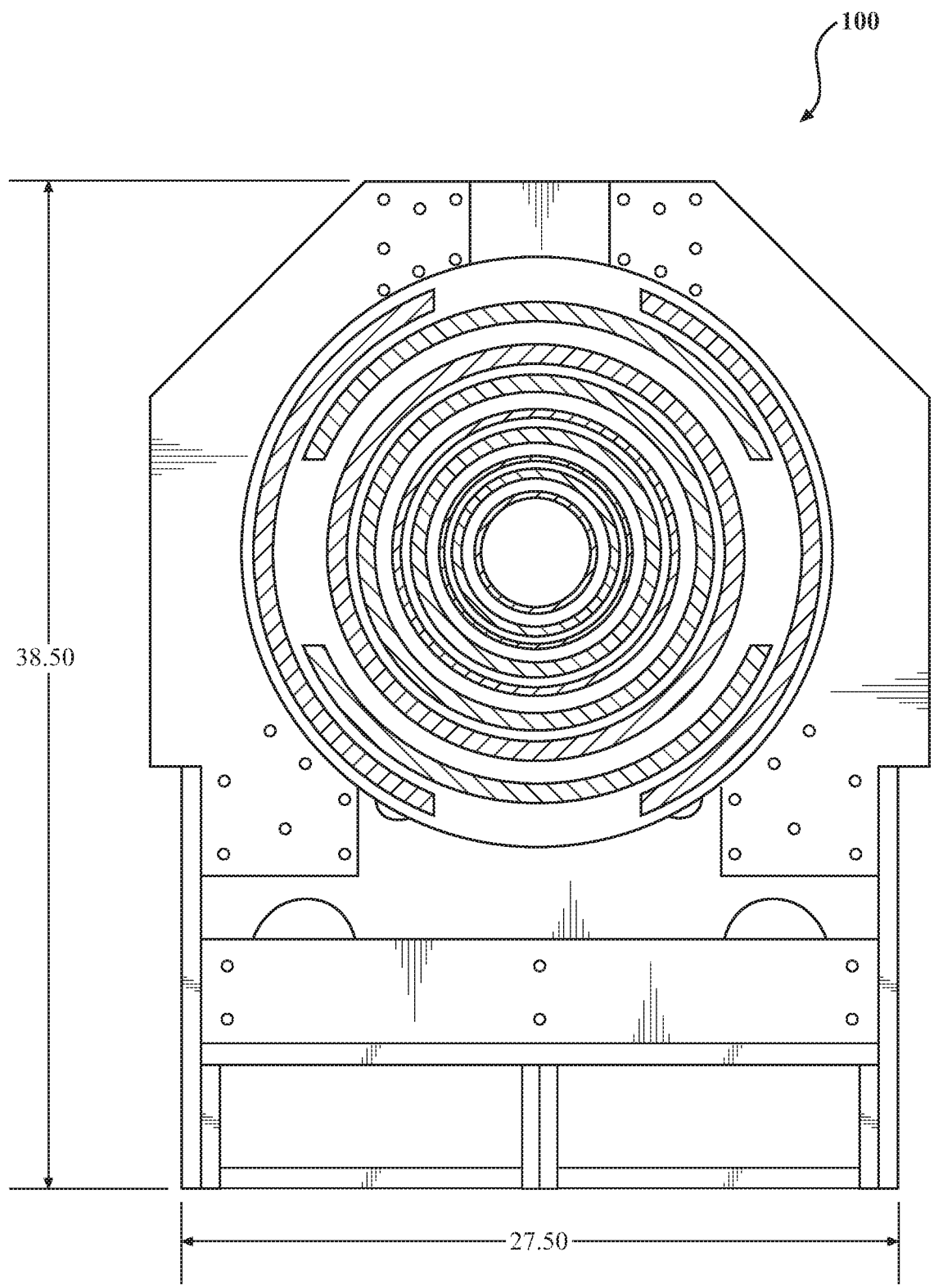
FIG. 4 is an elevational cross-sectional view of the PMRI system in accordance with an embodiment of the present invention.
Figure 5:
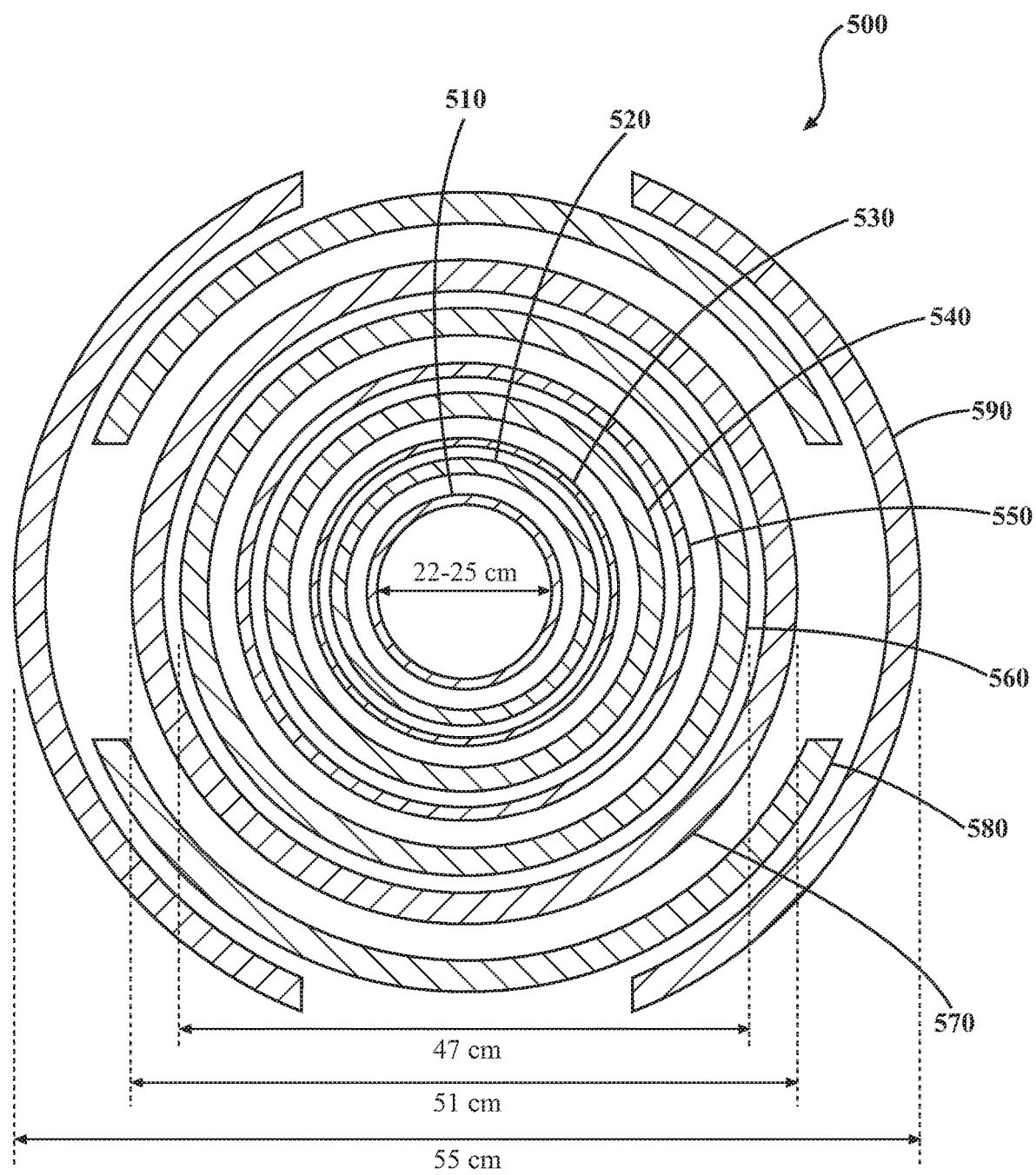
FIG. 5 is partial cross-sectional view of the PMRI system in accordance with an embodiment of the present invention.

According to one embodiment of the invention, the PMRI system, has the pre-pulse coil concentric with the inner transmitter/receiver coils as this configuration creates the maximum of the field strength. FIG. 4 shows the internal structure of the PMRI system with self-contained shielding. The internal structure will now be described in detail referring to FIG. 5. In this example, the PMRI system 500 includes a receiver coil 510, a transmitter coil 520, a pre-pulse Bp coil 540, a main magnetic Bm coil 560, Z-gradient coils 570, X-gradient coils 580, and Y-gradient coils 590. The dimensions in all figures are exemplary and not to scale. In this example, all the coils are concentric with each other.

A first shield 530 may be placed concentric with all the coils and disposed between the transmitter coil 520 and the Bp coil 540. To reduce noise, an optional second shielding 550 can be employed between the Bp and the Bra coils. Additionally, a third shielding 992 may be employed outside the gradient and Bin coils, as shown in FIG. 9.

Since the system does not have a lot of free space on the inside of the PMRI device and the coils have insulation that prevents electrical shorting into the shields, the two inner shields must fit inside the large coils and outside the smaller ones which they contain. The outermost shield could be at a range of values larger than the Bm coil.

Figure 8:
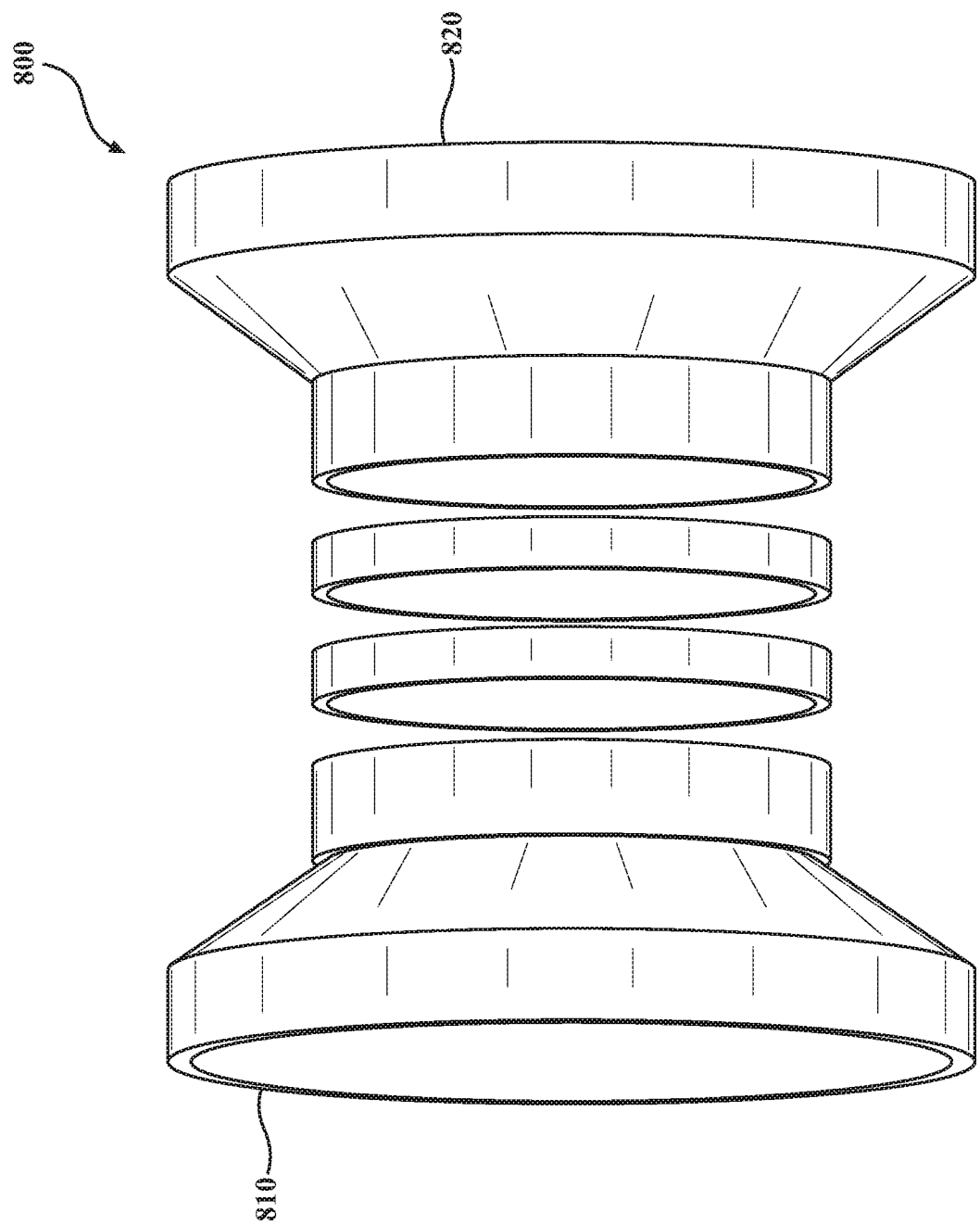
FIG. 8 is an illustration of a shield design with flared ends in accordance with an embodiment of the present invention.

In another embodiment, as shown in FIG. 8, the end of the device 810 and 820 may be flared where a larger child or adult, with shoulders wider than the internal bore, can rest for a head scan. If the end of the device is flared or funnel shaped, the shield arrangement would still be concentric, but the outermost shields flared, as in the embodiment discussed above.

Figure 9:
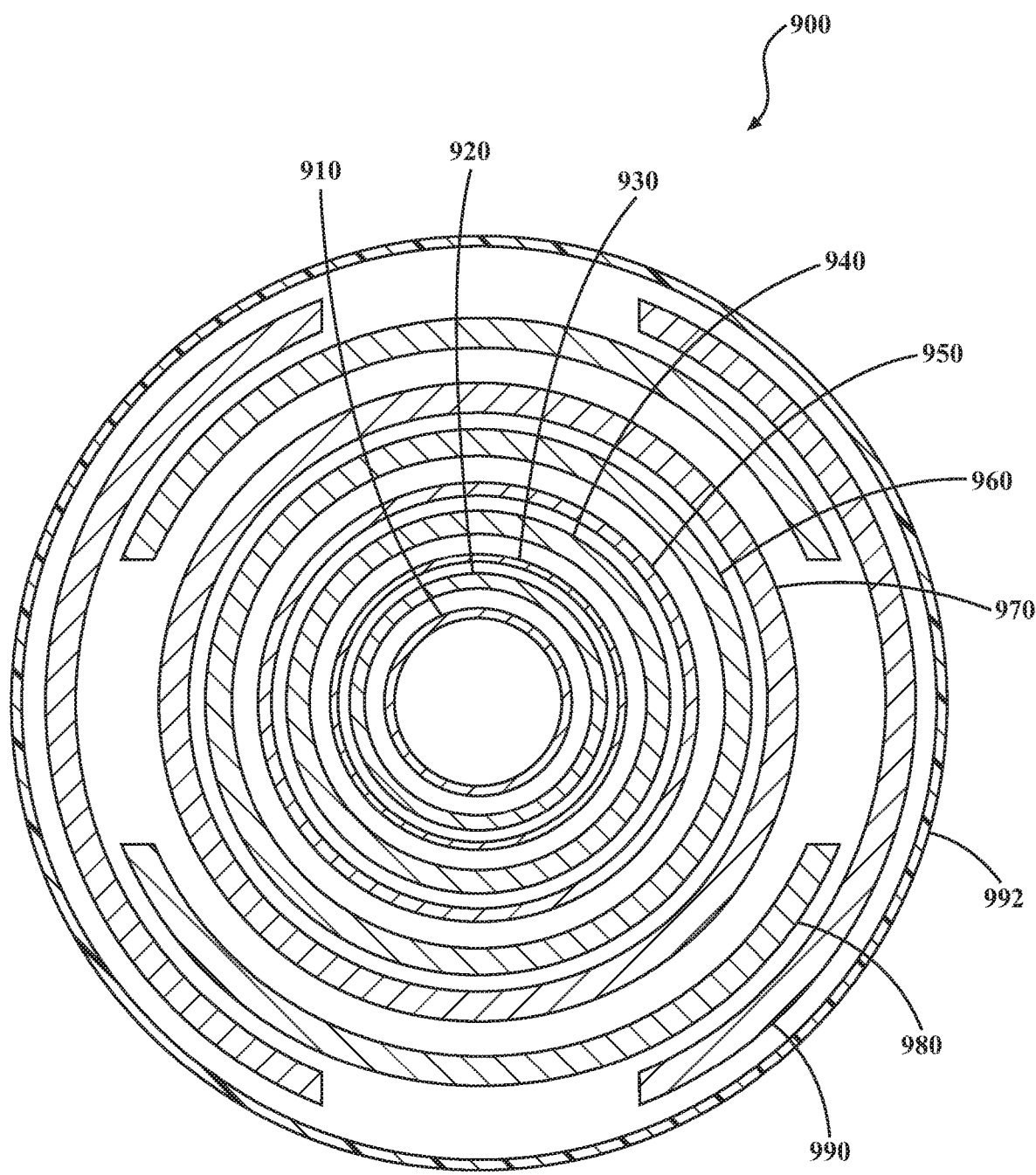
FIG. 9 is a partial cross-sectional view of the PMRI system in accordance with an embodiment of the present invention.

An alternative for the device is to use an inert but, very strong fiberglass cylinder of 'rocket tube' material to wrap the heavy coil (Bm and gradient) assembly around, as shown in FIG. 9. Similar to FIG. 5, the PMRI system 900 includes a receiver coil 910, a transmitter coil 920, a first shield 930, a pre-pulse Bp coil 940, a second shield 950, a main magnetic Bm coil 960, Z-gradient coils 970, X-gradient coils 980, and Y-gradient coils 990. A tube of material 992 can be created that would be both a structure tube and shielding, such as with aluminum honeycomb in the shape of a cylinder, that would wrap the PMRI system around.

Figure 10:
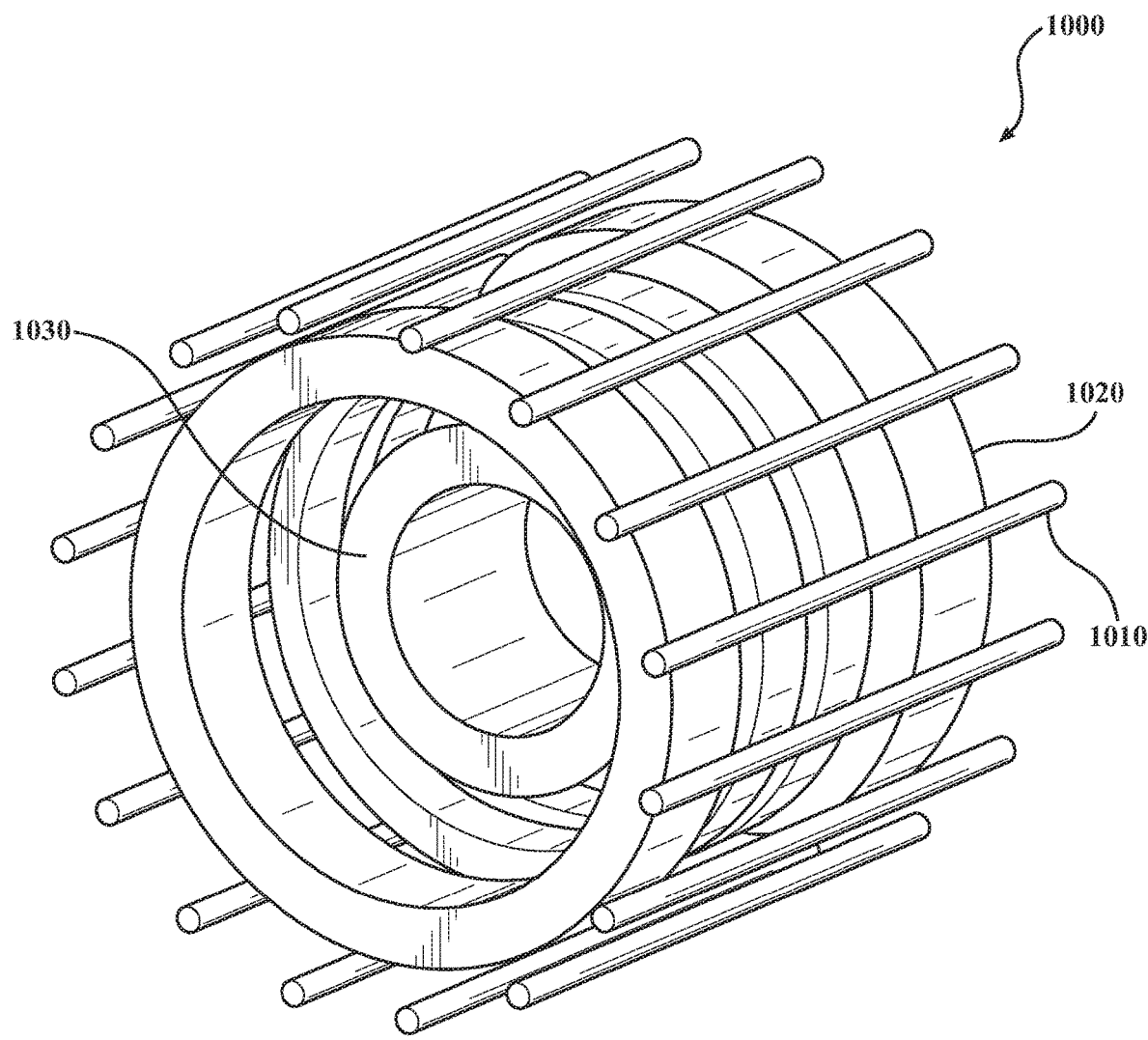
FIG. 10 is a perspective view of a shield design made of spaced rods.
Figure 11A:
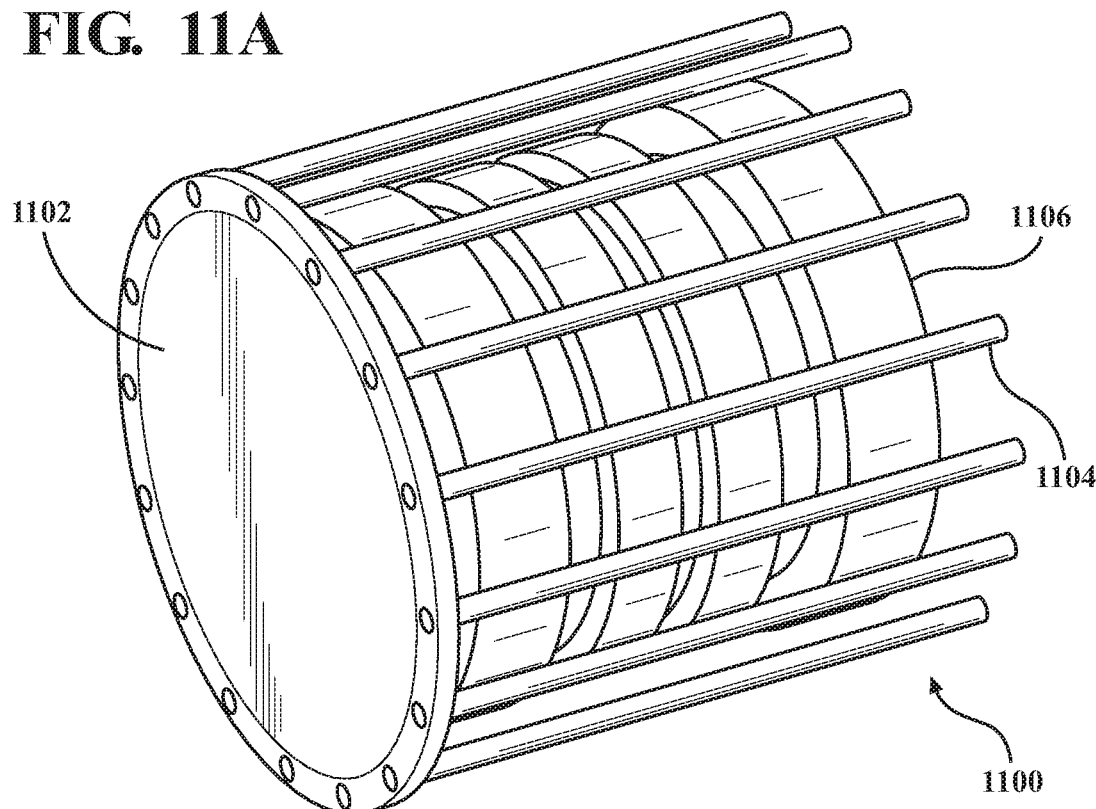
FIG. 11A is a perspective view of a shield design having a capped end.
Figure 11B:
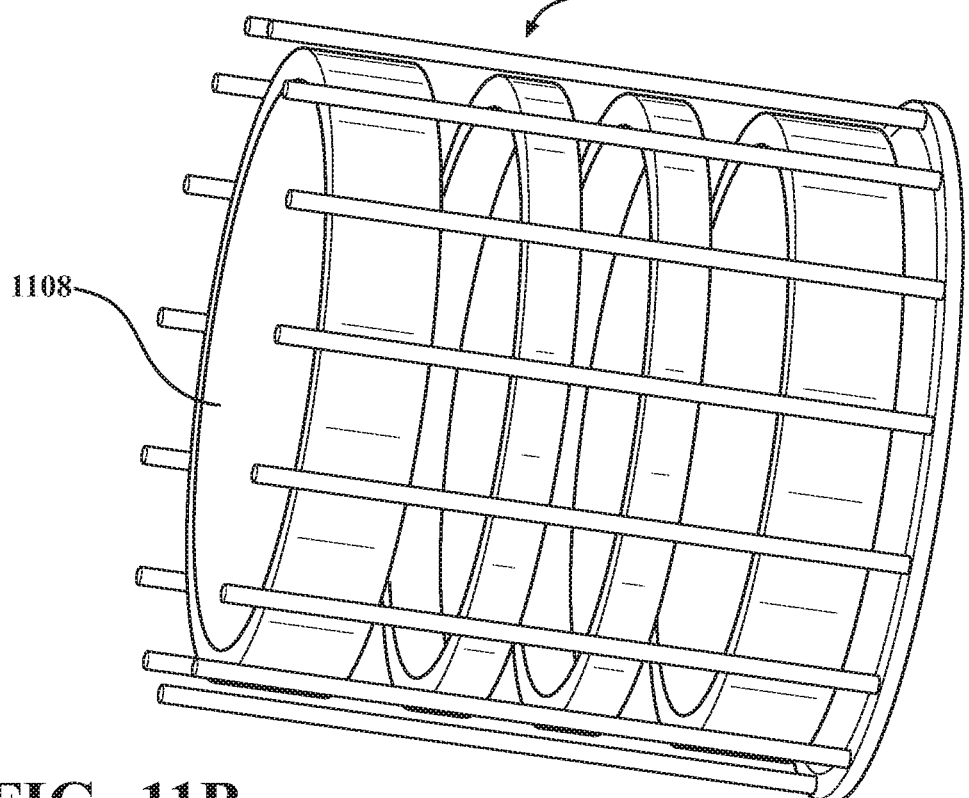
FIG. 11B is a perspective view of the shield design having a capped end from a different angle.

An alternative self-contained shield design is to have a cylindrical shield 1100 that has an open end 1106 for patient access, but a capped end 1102 away from the patient, as shown in FIGS. 11A and 11B. If made out of ferromagnetic material such as steel, such a shield will prevent the magnetic fields from straying out the closed end of the device, and boost the gradient field strength along the long axis (z axis) by two-fold—a boosted field strength with no additional power requirement. The only disadvantage of such an iron-based shield is that of weight. But this shield needs not be solid—bars 1104 as the walls of the cylinder will suffice if the spacing is well designed, and the end cap can have openings (not shown) in it for ventilation and airflow, because the temperature of the device needs to be kept within comfortable limits. FIG. 10 shows a shield design having bars 1010 as the walls of the cylinder, and without a capped end. The shield 1000 is supported by a plurality of $B_m$ coils 1020. A plurality of equally-spaced bars are attached to the outer perimeter of the $B_m$ coils 1020 and parallel to the axis of the coils 1020. The design may also include an inner shield 1030.

FIGS. 11A and 11B show a similar shield 1100 design as the shield 1000 in FIG. 10, except that the shield 1100 have a capped end 1102 on one end.

The shields may be grounded. Alternatively, the shields may be adaptively driven.

The integration of concentric shields with a PMRI system renders the PMRI system self contained in terms of shielding, making possible an inexpensive device, enabling mobility and portability of such systems.

Theory

In electromagnetic waves, there are electric fields and magnetic fields. In electric fields, it is possible to separate charges into positive and negative charges. For example using Gauss law, it can be shown that the electric field inside an enclosed conductive spherical volume is zero. This is because the charges enclosed within the volume will induce opposite charges on the inside surface of the sphere and these induced charges will in-turn induce charges of opposite polarity on the outside surface of the sphere. These charges generate electric fields which cancel each other resulting in no net electric field. This shows that it is possible to use conductive materials to separate electric charges and therefore provide shielding.

In this case, the conductivity of the material is important to provide free movement of electrons making charge separation easier. Magnetic fields, on the other hand, are more difficult to shield. Magnetic charges do not exist. Magnetic field lines run from the north pole and will always loop back to the south pole. It is therefore not possible to shield magnetic fields in the way the electric fields are shielded. However, using materials with high permeability, a conductive path can be selectively provided for magnetic fields to essentially direct them away from the volume of interest. On the other hand, Faraday's law explains the relation between magnetic and electric fields. Changing magnetic fields will induce currents on a conductive surface and these currents in turn generate magnetic fields in opposite direction. Therefore thin conductive materials with less permeability $\mu$ can also provide shielding for magnetic fields provided the frequency of the magnetic field is high enough to generate eddy currents on the surface of the material. This shielding increases with frequency.

The shielding effectiveness of a material needs therefore to be looked at separately in terms of electric fields and magnetic fields. The distance from the source generating electric or magnetic field is measured in terms of the wavelength $\lambda$. If the source of the field is less than $\lambda/2\pi$, the source is considered to be in the near field, and in the far field otherwise. Within the near field, the source of the field determines which field dominates. If the source is a dipole or monopole, the field generated is an electric field or high impedance field and if the source is a loop antenna, it generates mainly a magnetic field or low impedance field.

If the source is however in the far field, electromagnetic waves travel as plane waves and are mainly characterized by their wave impedance. The strengths of the magnetic and electric fields both decrease with increase in distance at the far field. As a result, plane waves are easily attenuated by any solid conducting metal and material thickness becomes insignificant with increase in frequency. Therefore, at high frequencies, any enclosed conductive material will be able to significantly shield plane waves.

Therefore, the shielding effectiveness of a material depends on the type of the field, the energy of the field and conductivity and permeability of the material. Shielding then results from reflection of incident RF energy from the surface of the material and absorption of RF energy as the wave travels through the material.

In our experiments according to one embodiment of the present invention, the following assumptions are made: 1. The shielding material is a good conductor which is grounded. This provides a direct path to the ground for any eddy currents generated on the surface of the material by the magnetic field. This limits the ability of the material to shield magnetic fields as the eddy currents will not be able to generate any opposing magnetic fields that would cancel the fringe fields being shielded against. 2. The frequency of our operation is in the kHz range. The magnetic shielding effectiveness, SE, of the material is highly dependent on frequency. Lower frequencies make it difficult for materials with low permeability to shield magnetic fields. 3. The source of wave is very close to the shield and is considered to be in the near field. The wave therefore is not fully developed into a plane wave.

With these assumptions, the shielding effectiveness SE of the material is then given as:

$$SE = 20 \log(4\eta_0/4\eta) + 20 \log e^{x/\delta} \quad (1.1)$$

where $\eta 0$ is the wave impedance of air and n is the wave impedance of the material, x is the material thickness and $\delta$ is the skin depth of the material and cart be estimated as $$|\eta| = \sqrt{\frac{\omega\mu}{\sigma}}$$

where $\sigma$ is the conductivity and $\mu$ is the permeability of the material. Equation 1.1 can be broken down into two parts as;

$$\text{Absorption loss} A \text{ (dB)} = 20 \log e^{x/\delta} \quad (1.2)$$

and $$\text{Reflection loss} R \text{ (dB)} = 20 \log(\eta_0/4\eta) \quad (1.3)$$

Using equations 1.2 and 1.3, theoretical graphs for the shielding effectiveness of aluminum and brass as a result of absorption and reflection losses are plotted. The thickness for the aluminum and brass materials used was 0.8128 mm, the conductivity for aluminum was $3.69 \times 10^7$ Siemens and for brass was $1.59 \times 10^7$ Siemens.

FIGS. 6A and 6B show the absorptive and reflective shielding effectiveness of aluminum and brass respectively.

As can be seen from the graphs, as the frequency increases, absorption loss in the material reduces. This is because the wavelength becomes smaller and is able to interact and penetrate the material with little attenuation. On the other hand, the reflection losses increase because of the same reason. The smaller wavelength allows the wave to bounce off the material many times increasing the probability of reflection. The total shielding effectiveness is the sum of the absorption loss and reflection loss.

Fabrication of Shields of the RF Shields

Figure 7:
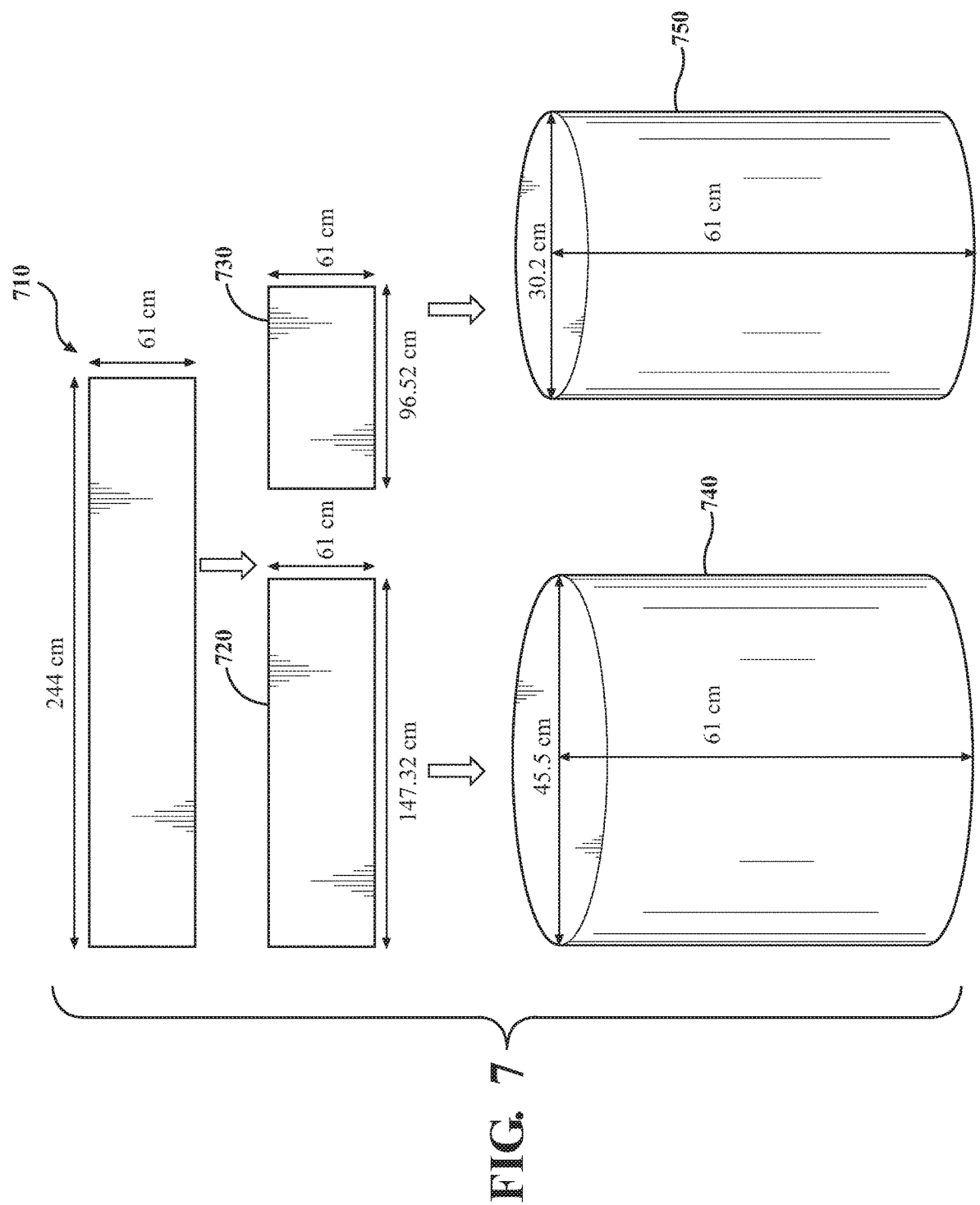
FIG. 7 is a schematic illustration of the steps in the fabrication of a shield in accordance with an embodiment of the present invention.

According to one embodiment of the present invention, two types of radio frequency shields are fabricated out of aluminum and brass. In this example, two shields were fabricated using aluminum 6061 and brass alloy which were purchased from McMaster Can (http://www.mernaster-.com/). The thickness of both materials 710 was 0.8128 mm, length was 2.44 m and width was 0.61 m. Each material was cut into two pieces of length 147.32 cm for 720 and 96.52 cm for 730. Each of the pieces was then rolled up end-to-end to form two cylinders 740, 750 of diameters 45.52 cm and 30.24 cm as shown in FIG. 7. To maintain electrical contact, the seam was livened using rivets of matching material (i.e. brass rivets for brass shield). Rivets were attached at every 100 mm.

Experimental Set-Up to Test the Shielding Effectiveness of the Shields

Figure 12:
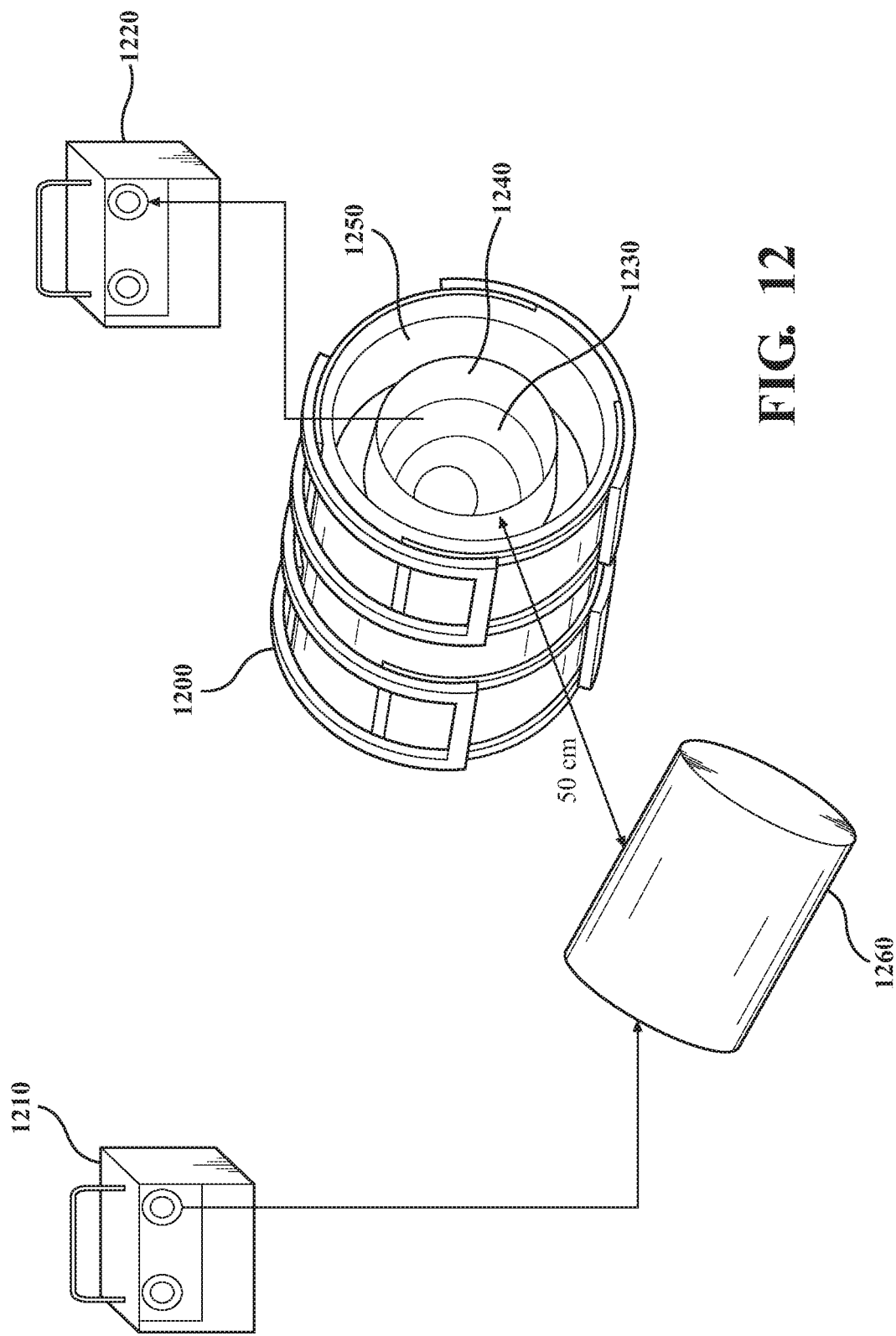
FIG. 12 is schematic view of an experimental set-up.

In the experimental set-up, as shown in FIG. 12, a transmit coil 1260 was connected to a function generator 1210 and located outside the MRI system 1200, 0.5 m from the shield 1240. The receiver coil 1230 was connected to a spectrum analyzer 1220 and inserted inside the MRI system 1200. Sinusoidal waveforms at amplitudes of 2.5 mV peak-peak were generated using the function generator 1210 and broadcast using the transmit coil 1260. The receiver coil 1230, acting as receiver antenna, detects the amplitude and frequency of the transmitted wave and the spectrum analyzer 1220 is used to display these parameters. This was done when the system was shielded using aluminum, brass and when the system was not shielded. The sinusoidal signal was broadcast at different frequencies ranging from 50 kHz to 500 kHz and each time the amplitude of the signal was recorded.

To test the shielding effectiveness, a known sinusoidal waveform was transmitted using a radio frequency coil and the transmitted signal was detected using a partially shielded tin-tuned coil. The same signal was also detected using an un-shielded coil. A comparison of the two signals showed that the signal amplitude dropped significantly when the coil was partially shielded. Partial shielding was used in order to mimic the real situation where access to the imaging volume has to be allowed.

Results and Discussion

Figures 13A, 13B:
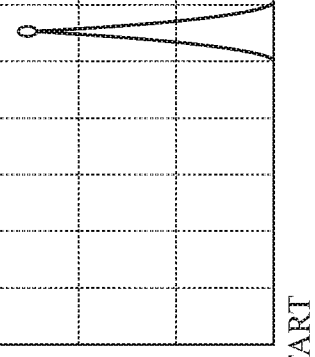
FIG. 13A is a schematic view showing a signal before shielding.
FIG. 13B is a schematic view showing an attenuated signal after shielding.

FIGS. 13A and 13B are schematic photo screens of the spectrum analyzer showing amplitude of the wave detected before shielding and after shielding. It can be seen that the transmitted wave is significantly attenuated by the shielding material.

Figure 14:
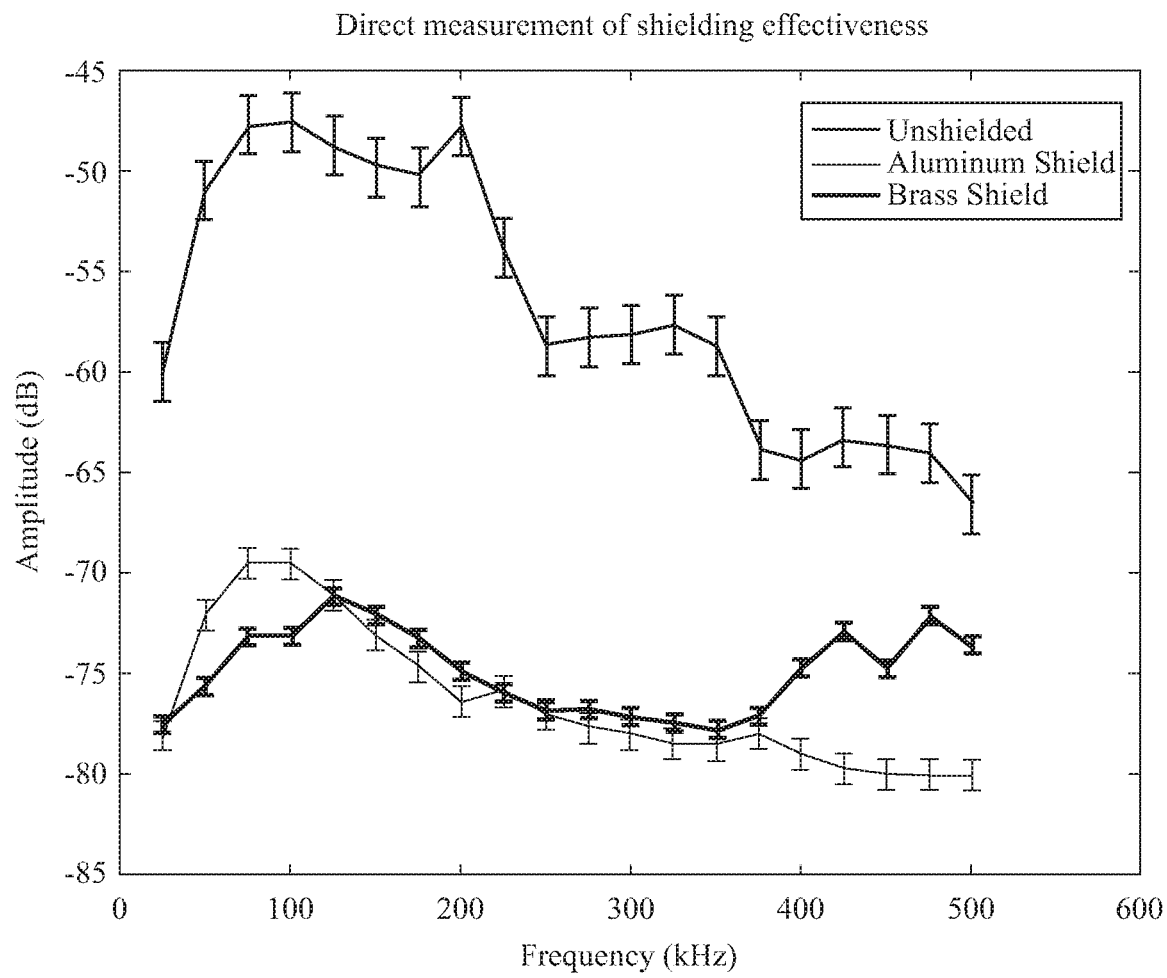
FIG. 14 is a graph showing experimental results of direct measurement of shielding effectiveness.

FIG. 14 shows the results measured using the spectrum analyzer for the shield effectiveness of aluminum and brass.

As predicted in the theory, it can be seen that at low frequencies, the wavelength is so large that the probability of the wave being incident on the surface of the shield is low. The absorptive and reflective losses are therefore very low. However as frequency increases, the wave can interact with the shielding material and the shielding effectiveness is seen to increase. This is shown in the graphs by the decrease in the amplitude of the signal detected. At higher frequencies, shielding is mostly as a result of reflection rather than both reflection and absorption. The shielding effectiveness of the materials, especially brass in this case is seen to reduce at frequencies beyond 400 kHz.

From the graph, it can be inferred that aluminum is a better shielding material than brass. This could be because of its higher electrical conductivity which contributes to absorption losses. For the frequency between 120 kHz and 300 kHz, either material can be used as RF shield.

The amplitude of background signal recorded was −80 dB. The Military Standard Handbook 419A suggests that shielding effectiveness of up to 80 dB is adequate enough for most applications.

The invention claimed is:

1. An ultra-low field pre-pulse Magnetic Resonance Imaging (PMRI) system for a head, comprising:
    annular RF coils defining a bore having an opening for access of the head;
    a pre-pulse coil substantially surrounding the RF coils;
    a coil assembly including a main magnetic field coil and a plurality of gradient coils surrounding the pre-pulse coil; and
    a first cylindrical shield concentric with the RF coils, the first cylindrical shield partially surrounding the RF coils and being disposed inside the pre-pulse coil for shielding the RF coils from environmental electromagnetic disturbances, the first cylindrical shield made from conductive materials.

2. The PMRI system according to claim 1, further comprising a second cylindrical shield concentric with the first cylindrical shield, partially surrounding the pre-pulse coil, and being disposed inside the coil, assembly.

3. The PMRI system according to claim 2, further comprising a third cylindrical shield concentric with the first and second cylindrical shields and substantially surrounding the coil assembly.

4. The PMRI system according to claim 3, wherein the third cylindrical shield includes a wall formed of spaced bars.

5. The PMRI system according to claim 3, wherein the third cylindrical shield is made from ferromagnetic materials.

6. The PMRI system according to claim 1, wherein an open end of the first cylindrical shield is flared for a larger child or adult with shoulders wider than the bore.

7. The PMRI system according to claim 1, wherein the first cylindrical shield is passive.

8. The PMRI system according to claim 1, wherein the first cylindrical shield is grounded.

9. The PMRI system according to claim 1, wherein the first cylindrical shield is driven adaptively.

10. The PMRI system according to claim 1, wherein the first cylindrical shield has an open end for the head access and a capped end away from the open end.

11. The PMRI system according to claim 1, wherein the first cylindrical shield is made from aluminum or brass.

* * * * *